(12) United States Patent  
Ojala et al.

(10) Patent No.: US 8,896,820 B2  
(45) Date of Patent: Nov. 25, 2014

(54) OPTICAL MEASUREMENT INSTRUMENT

(75) Inventors: Markku Ojala, Turku (FI); Jyrki Laitinen, Kuusisto (FI); Christer Isaksson, Turku (FI); Tommi Elo, Turku (FI)

(73) Assignee: Wallac Oy, Turku (FI)

( * ) Notice: Subject to any disclaimer, the term of this patent is extended or adjusted under 35 U.S.C. 154(b) by 378 days.

(21) Appl. No.: 13/500,333

(22) PCT Filed: Oct. 6, 2010

(86) PCT No.: PCT/FI2010/050774  
§ 371 (c)(1),  
(2), (4) Date: Jun. 7, 2012

(87) PCT Pub. No.: WO2011/042602  
PCT Pub. Date: Apr. 14, 2011

(65) Prior Publication Data  
US 2012/0240692 A1 Sep. 27, 2012

(30) Foreign Application Priority Data  
Oct. 6, 2009 (FI) .................................... 20096021

(51) Int. Cl.  
*G01N 21/01* (2006.01)  
*G01N 21/64* (2006.01)  
*G01N 21/03* (2006.01)

(52) U.S. Cl.  
CPC ........ *G01N 21/6452* (2013.01); *G01N 21/0332* (2013.01); *G01N 2201/0231* (2013.01)  
USPC ............................................ 356/36; 356/246

(58) Field of Classification Search  
CPC .......... G01N 21/0332; G01N 21/6452; G01N 2201/0231  
USPC .................... 356/36, 244, 246, 929, 949, 951  
See application file for complete search history.

(56) References Cited

U.S. PATENT DOCUMENTS 2,272,836 A * 2/1942 Gerdien ........................ 600/494  
2,759,354 A * 8/1956 Cherry et al. ................. 73/25.02  
(Continued)

FOREIGN PATENT DOCUMENTS

DE 2629051 A * 1/1978 ............. G01N 25/18  
EP 0 576 291 12/1993  
(Continued)

OTHER PUBLICATIONS

International Preliminary Report on Patentability for PCT/FI2010/050774, report issued Apr. 11, 2012.*

(Continued)

*Primary Examiner* — Thomas P Noland  
(74) *Attorney, Agent, or Firm* — Young & Thompson (57) ABSTRACT

An optical measurement instrument includes: an excitation light source (120) arranged to produce an excitation beam for at least one of samples to be measured and a detector (132) arranged to detect an emission beam emitted by one of the samples to be measured and to produce a detection signal responsive to the detected emission beam. The optical measurement instrument further includes an arrangement for controlling temperature of the samples to be measured. The arrangement includes: one or more temperature sensors (176) for producing one or more temperature signals responsive to temperature of a measurement chamber (170) of the optical measurement instrument, one or more heating resistors (171-175) arranged to warm the measurement chamber, and a controller (177) arranged to control electrical power supplied to the heating resistors on the basis of the one or more temperature signals.

14 Claims, 5 Drawing Sheets

(56) References Cited

U.S. PATENT DOCUMENTS

| | | | |
|---|---|---|---|
| 2,763,151 A * | 9/1956 | Richardson | 73/25.02 |
| 3,007,333 A * | 11/1961 | Chadenson | 73/25.01 |
| 3,763,422 A * | 10/1973 | MacPhee et al. | 324/438 |
| 3,825,725 A | 7/1974 | Leitner et al. | |
| 4,165,631 A * | 8/1979 | Boinet et al. | 73/54.01 |
| 4,652,127 A | 3/1987 | Ekholm et al. | |
| 5,207,987 A | 5/1993 | Kureshy et al. | |
| 5,756,878 A * | 5/1998 | Muto et al. | 73/25.03 |
| 6,151,111 A | 11/2000 | Wechsler et al. | |
| 6,977,722 B2 | 12/2005 | Wohlstadter et al. | |
| 8,746,008 B1 * | 6/2014 | Mauritsen et al. | 356/246 X |
| 2004/0083789 A1 * | 5/2004 | Stark et al. | 73/25.02 |
| 2004/0241691 A1 | 12/2004 | Baechi | |
| 2005/0142033 A1 | 6/2005 | Glezer et al. | |
| 2008/0255683 A1 | 10/2008 | Takahashi et al. | |
| 2011/0042582 A1 * | 2/2011 | Ingber et al. | 356/246 X |
| 2011/0042583 A1 * | 2/2011 | Chang | G01N 21/64 |
| 2012/0118291 A1 * | 5/2012 | Brodkin et al. | 128/205.23 |

FOREIGN PATENT DOCUMENTS

| | | | |
|---|---|---|---|
| EP | 1 541 237 | 6/2005 | |
| EP | 1 647 868 | 4/2006 | |
| EP | 1 704 922 | 9/2006 | |
| FR | 2735866 A1 * | 12/1996 | G01N 27/407 |
| GB | 761967 A * | 11/1956 | G01N 27/24 |
| SU | 763791 A1 * | 9/1980 | G01N 33/04 |
| WO | WO 2007074021 A1 * | 7/2007 | G01N 27/407 |
| WO | 2008/024821 | 2/2008 | |

OTHER PUBLICATIONS

International Search Report dated Feb. 10, 2011, corresponding to PCT/FI2010/050774, 5 pages, Written Opinion not included.

Finnish Search Report dated Jun. 3, 2010, corresponding to the Foreign Priority Application No. 20096021, 2 pages.

* cited by examiner

OPTICAL MEASUREMENT INSTRUMENT

FIELD OF THE INVENTION

The invention relates to a method for controlling temperature of samples being measured with an optical measurement instrument. Furthermore, the invention relates to a base module for an optical measurement instrument. The base module can be used as a platform with the aid of which different optical measurement instruments provided with measurement temperature control can be constructed using different optical measurement elements such as for example lenses, fibres, detectors, light sources, etc. An optical measurement can be, for example but not necessarily, an absorption measurement, a photoluminescence measurement, or a chemiluminescence measurement. Furthermore, the invention relates to an optical measurement instrument.

BACKGROUND

The work in analytical biochemical laboratories and in clinical laboratories is often based on different tags or labels coupled on macromolecules under inspection. Typical labels used are different radioactive isotopes, enzymes, different fluorescent molecules and e.g. fluorescent chelates of rare earth metals. Detection of enzyme labels can be performed by utilizing its natural biochemical function, i.e. to alter the physical properties of molecules. In enzyme immunoassays colourless substances are catalysed by enzyme to colourful substances or non-fluorescent substances to fluorescent substances. The colourful substances can be measured with absorption measurement, i.e. photometric measurement. In the absorption measurement the intensity of filtered and stabilized beam is first measured without any sample and then the sample inside one plate is measured. The absorbance i.e. the absorption values are then calculated.

The fluorescent substances can be measured with fluorescent measurement that is generally used for measuring quantities of fluorescent label substance in a sample. The most photoluminescence labels are based on molecular photoluminescence process. In this process optical radiation is absorbed by the ground state of a molecule. Due to the absorption of energy the quantum molecule rises into higher excited state. After the fast vibrational relaxation the molecule returns back to its ground state and the excess energy is released as an optical quantum. Due to losses in this process the average absorbed energies are higher than the average emitted energies. A further measurement method is chemiluminescence measurement where emission of a substance is measured from a sample without excitation by illumination. Thus a photoluminometer suitable for photoluminescence measurements can also be used as a chemiluminometer.

Further, there is an analysing method called Amplified Luminescent Proximity Homogeneous Assay or AlphaScreen™. The function of the AlphaScreen™ method is based on the use of small beads that attach to the molecules under study. There are two types of beads that are coated with a material acting either as a donor or acceptor of singlet-state oxygen. The measurement starts, when the liquid sample is illuminated by light with a suitable wavelength e.g. 680 nm. After this, the material in the donor bead converts ambient oxygen into singlet-state oxygen. The single-state molecules have a short lifetime and they can reach only about a 200 nm distance by diffusion in the liquid. If the chemical reaction in question has taken place, both the donor and acceptor beads are bound to the same molecule and so they are sufficiently close to each other. In this case the singlet-state oxygen may reach the acceptor bead where a series of reactions is started. As the last phase of the reaction the coating material in the acceptor beads emits photons in the 500-700 nm range. If the chemical reaction has not taken place the singlet-state oxygen cannot reach the acceptor bead and the emission light is not detected. By measuring the intensity of light it is possible to conclude the efficiency of the chemical reaction.

An optical measurement instrument suitable for performing some or all of the measurements of the kind described above comprises typically at least one excitation light source for producing excitation beams to one or more samples to be measured at each time. Each excitation light source can be for example a flash lamp or a laser source. An optical path from an excitation light source to a sample may contain for example lenses, fibers, mirrors, dichroic mirrors, optical filters, monochromators and/or other optical elements. The optical measurement instrument further comprises at least one detector for detecting emission beams emitted by the samples to be measured at each time, and for producing detection signals responsive to the detected emission beams. Each detector can be for example a photo-diode or a photo-multiplier tube. An optical path from the sample to the detector may contain for example lenses, fibers, mirrors, dichroic mirrors, optical filters, monochromators, and/or other optical elements. The optical measurement instrument may further comprise a processing device for producing a measurement result for each sample to be measured on the basis of the detection signal related to that sample.

The optical measurement instrument comprises a reception device for receiving samples to be measured. Each sample to be measured is stored in one of a plurality of sample wells that are built on e.g. a microtitration plate or some other sample support element. The reception device can be, for example, a movable sledge adapted to receive the microtitration plate or the other sample support element. Due to the fact that the reception device allows moving the microtitration plate or the other sample support element, the samples can be measured in a temporally successive manner so that each sample is in turn the sample that is currently being measured. In order to maximize quality of the measurement results obtained with the optical measurements, temperature of the samples being measured is tried to be kept as close as possible to an optimum measurement temperature.

Publication U.S. Pat. No. 6,977,722 discloses an optical measurement instrument that includes an enclosure that is arranged to surround a reception device for receiving samples to be measured. The enclosure constitutes a measurement chamber arranged to protect the samples to be measured against undesired stray light and thermal radiation from the surroundings, and thus, inter alia, to keep the samples at a relatively steady temperature. An inconvenience related to the construction described above is that the temperature in the measurement chamber may, however, slowly wander along with changes of the temperature of the surroundings.

SUMMARY

In accordance with a first aspect of the invention, there is provided a new optical measurement instrument. The optical measurement instrument according to the invention comprises:
   optical measurement elements including an excitation light source arranged to produce an excitation beam for at least one of samples to be measured and a detector arranged to detect an emission beam emitted by one of the samples to be measured and to produce a detection signal responsive to the detected emission beam, a mechanical structure for forming a measurement chamber and for supporting one or more of the optical measurement elements, a reception device inside the measurement chamber for receiving the samples to be measured, heating resistors placed at different places of the measurement chamber and arranged to warm the measurement chamber, at least one temperature sensor arranged to produce a temperature signal responsive to temperature of the measurement chamber, and a controller arranged to control electrical powers supplied to the heating resistors on the basis of the temperature signal, wherein the controller is arranged to control the electrical powers supplied to the heating resistors so that the electrical power supplied to a first one of the heating resistors is proportional to $B_1 \times q$ and the electrical power supplied to a second one of the heating resistors is proportional to $B_2 \times q$, wherein q is a quantity controlled on the basis of one of the at least one temperature signal, $B_1$ is a pre-determined balancing coefficient specific to the first one of the heating resistors, and $B_2$ is a pre-determined balancing coefficient specific to the second one of the heating resistors, the balancing coefficient $B_1$ having a different value than the balancing coefficient $B_2$ in order to compensate effect of differences in temperature/power-characteristics related to surroundings of the first and second ones of the heating resistors.

As the temperature of the measurement chamber is actively controlled with the aid of the heating resistors, the at least one temperature sensor, and the controller, the measurement chamber can be more easily kept at a desired temperature than in conjunction with the optical measurement instrument according to the prior art described earlier in this document. Value of each balancing coefficient depends on temperature/power-characteristics related to surroundings of the respective heating resistor. With the aid of the balancing coefficients, it is possible to achieve a desired temperature distribution (e.g. a flat temperature distribution) in a measurement chamber also in case where the temperature is measured only from a single spot. Values of the balancing coefficient may be different for different temperatures and/or temperature distributions. Hence, a desired temperature distribution can be achieved without a need for multiple measurements and multivariable control systems where the power sharing between heating resistors has to be determined on-line during operation of a measurement instrument.

In accordance with a second aspect of the invention, there is provided a new base module for an optical measurement instrument. The base module can be used as a platform with the aid of which different optical measurement instruments provided with measurement temperature control can be constructed using different optical measurement elements such as for example lenses, fibres, detectors, light sources, etc. The base module according to the invention comprises:

a mechanical structure for forming a measurement chamber and for supporting one or more optical measurement elements, a reception device inside the measurement chamber for receiving samples to be measured, heating resistors placed at different places of the measurement chamber, each heating resistor being arranged to warm the measurement chamber, at least one temperature sensor, each temperature sensor being arranged to produce a temperature signal responsive to temperature of the measurement chamber, and a controller arranged to control electrical power supplied to each of the at least one heating resistor on the basis of the at least one temperature signal produced by the at least one temperature sensor, wherein the controller is arranged to control the electrical powers supplied to the heating resistors so that the electrical power supplied to a first one of the heating resistors is proportional to $B_1 \times q$ and the electrical power supplied to a second one of the heating resistors is proportional to $B_2 \times q$, wherein q is a quantity controlled on the basis of one of the at least one temperature signal, $B_1$ is a pre-determined balancing coefficient specific to the first one of the heating resistors, and $B_2$ is a pre-determined balancing coefficient specific to the second one of the heating resistors, the balancing coefficient $B_1$ having a different value than the balancing coefficient $B_2$ in order to compensate effect of differences in temperature/power-characteristics related to surroundings of the first and second ones of the heating resistors.

The base module may preferably but not necessarily further comprise a controller arranged to control electrical power supplied to each of the at least one heating resistor on the basis of the temperature signal.

In accordance with a third aspect of the invention, there is provided a new method for controlling temperature of samples being measured with an optical measurement instrument. The method according to the invention comprises:

producing, with at least one temperature sensor, a temperature signal responsive to temperature of a measurement chamber of the optical measurement instrument, the samples being located in the measurement chamber, controlling electrical powers supplied to heating resistors placed at different places of the measurement chamber on the basis of the temperature signal, and warming the measurement chamber with the heating resistors, wherein the electrical powers supplied to the heating resistors are controlled so that the electrical power supplied to a first one of the heating resistors is proportional to $B_1 \times q$ and the electrical power supplied to a second one of the heating resistors is proportional to $B_2 \times q$, wherein q is a quantity controlled on the basis of one of the at least one temperature signal, $B_1$ is a pre-determined balancing coefficient specific to the first one of the heating resistors, and $B_2$ is a pre-determined balancing coefficient specific to the second one of the heating resistors, the balancing coefficient $B_1$ having a different value than the balancing coefficient $B_2$ in order to compensate effect of differences in temperature/power-characteristics related to surroundings of the first and second ones of the heating resistors.

A number of exemplifying embodiments of the invention are described in accompanied dependent claims.

Various exemplifying embodiments of the invention both as to constructions and to methods of operation, together with additional objects and advantages thereof, will be best understood from the following description of specific exemplifying embodiments when read in connection with the accompanying drawings.

The verbs "to comprise" and "to include" are used in this document as open limitations that neither exclude nor require the existence of unrecited features. The features recited in depending claims are mutually freely combinable unless otherwise explicitly stated.

BRIEF DESCRIPTION OF THE FIGURES

The exemplifying embodiments of the invention and their advantages are explained in greater detail below in the sense of examples and with reference to the accompanying drawings, in which.

DESCRIPTION OF THE EMBODIMENTS

Figure 1A:
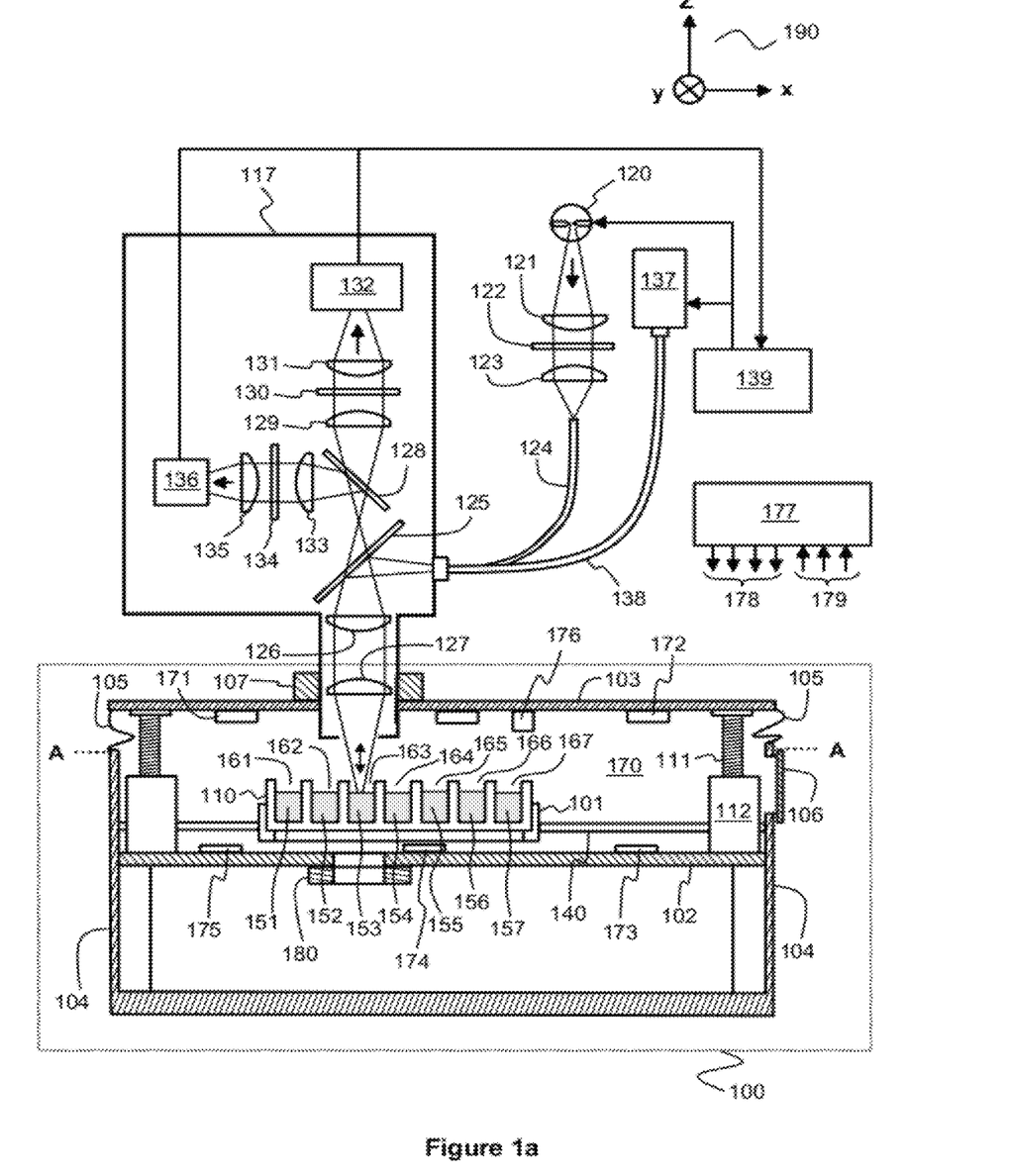
FIG. 1a shows a schematic illustration of a section view of an optical measurement instrument according to an embodiment of the invention.

FIG. 1a shows a schematic illustration of a side view of an optical measurement instrument according to an embodiment of the invention. The optical measurement instrument includes a base module 100 that includes a mechanical structure that forms a measurement chamber 170 and acts as a support onto which one or more optical measurement elements can be mounted. The mechanical structure forming the measurement chamber 170 includes a first plate 102 and a second plate 103 that is substantially parallel and, in a direction perpendicular to the first plate, overlapping with the first plate. The second plate 103 is movably supported with respect to the first plate 102 so that the second plate is movable in the direction substantially perpendicular to the first and second plates, i.e. the second plate is movable in the positive and negative z-directions of the co-ordinate system 190. The second plate 103 is movably supported to the first plate 102 with threaded rods and with respective counterparts. Reference numbers 111 and 112 indicate one of the threaded rods and its respective counterpart, respectively. It is also possible to support the second plate 103 movably with respect to the first plate 102 e.g. with the aid of toothed bars and respective gearwheels as counterparts of the toothed bars. The counterparts can be provided, for example, with servomotors arranged to move the second plate 103 in the positive or negative z-direction. The mechanical structure forming the measurement chamber further includes walls 104 extending from outer edges of the first plate to outer edges of the second plate. In the exemplifying embodiment shown in FIG. 1a, the said walls include a flexible portion 105 fastened to outer edges of the second plate 103. The flexible portion 105 allows the movement of the second plate relative to the first plate. It would be also possible to provide the second plate 103 e.g. with walls protruding towards the negative z-direction, overlapping the walls 104, and being capable of sliding with respect to the walls 104 thus allowing the movement of the second plate relative to the first plate. The optical measurement instrument includes, inside the measurement chamber 170, a reception device 101 for receiving samples 151, 152, 153, 154, 155, 156, 157 to be measured. The measurement chamber 170 is capable of protecting the samples against adverse stray light and thermal radiation from the surroundings. The walls 104 include a door element 106 for enabling insertion of the samples to be measured into the measurement chamber. The second plate 103 includes a fastening interface 107 provided with an aperture. The fastening interface is suitable for an optical measurement element 117 that is mounted to the second plate 103. The distance between the optical measurement element 117 and the sample being measured can be adjusted by moving the second plate 103 in the positive or negative z-direction. Also the first plate 102 includes a fastening interface 180 provided with an aperture and suitable for an optical measurement element. In the configuration shown in FIG. 1a, there is however no optical measurement element mounted to the fastening interface 180.

Figure 1B:
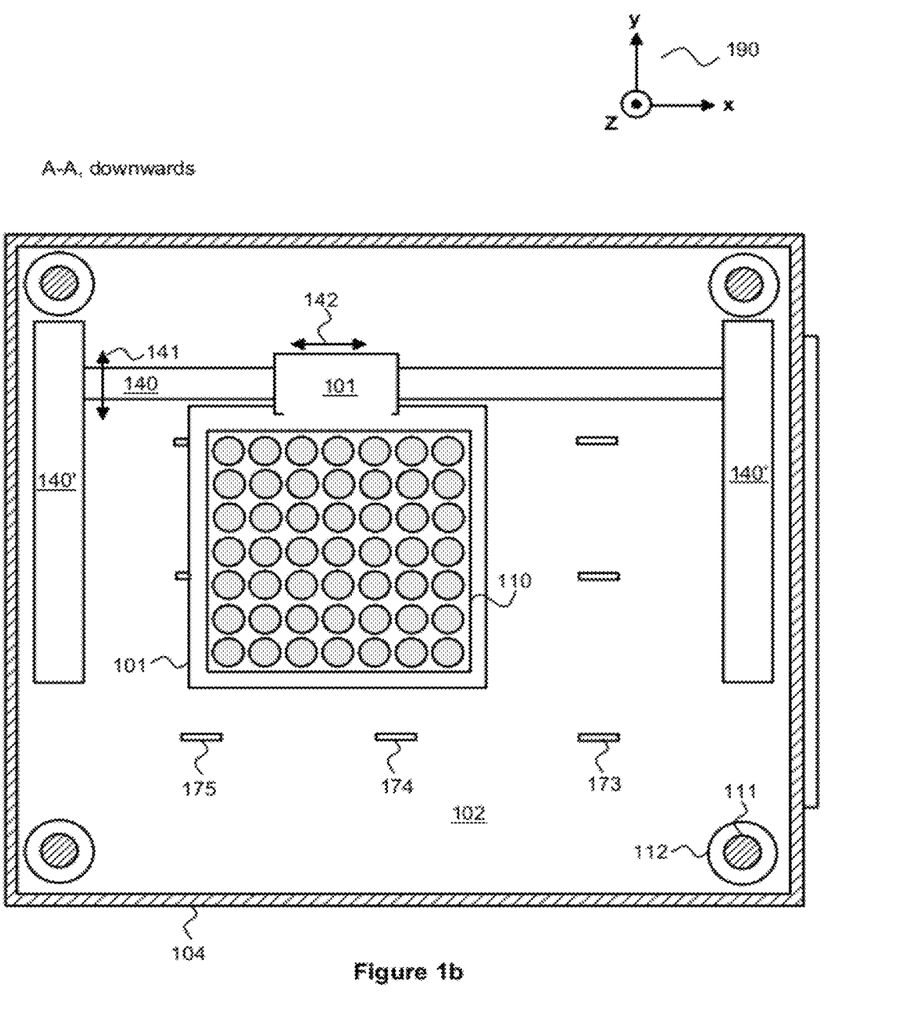
FIG. 1b shows a schematic illustration of a view seen downwards from line A-A of FIG. 1a, FIG. 1c shows a schematic illustration of a view seen upwards from the line A-A of FIG. 1a, FIG. 2 shows a schematic illustration of a section view of a base module according to an embodiment of the invention.

The samples 151, 152, 153, 154, 155, 156, 157 to be measured are stored in sample wells 161, 162, 163, 164, 165, 166, 167, respectively. FIG. 1b shows a schematic illustration of a view seen downwards from line A-A of FIG. 1a. As can be seen from FIG. 1b, the sample wells constitute in this exemplifying case a 7×7 array. In many cases there are, however, more sample wells in the array, e.g. 96 sample wells. The reception device 101 has an interface for receiving a changeable separate element 110, e.g. a microtitration plate, which includes the plurality of the sample wells. The reception device 101 is often called a sample plate sledge. The reception device 101 is mechanically connected to a support rail 140 that is supported by support elements 140' in such a manner that the support rail 140 is movable in the directions defined by a two-headed arrow 141 shown in FIG. 1b. The reception device 101 is in turn movable along the support rail 140 in the directions defined by a two-headed arrow 142 shown in FIG. 1b. Hence, the reception device 101 and thus also the sample wells are movable in parallel with the first and second plates 102 and 103, i.e. the reception device 101 and the sample wells are movable in the xy-plane defined by the co-ordinate system 190. Thus, each sample can be measured in its turn by changing the mechanical position of the reception device 101. In the exemplifying situation shown in FIG. 1a, a sample that is currently being measured is the sample 153 that is stored in the sample well 163. In principle it would be possible that the element 110 including the sample wells is an integral part of the reception device, i.e. the reception device would include the sample wells, but several advantages are provided by having a changeable element that includes the plurality of sample wells.

Referring to FIG. 1a, the optical measurement instrument includes an excitation light source 120 that is arranged to produce an excitation light beam. The excitation light source 120 can be, for example, a flash lamp. The excitation light beam radiated by the excitation light source 120 is collimated with a lens 121 and directed through an optical filter 122. Different optical filters can be selected for different wavelengths. The excitation light beam is then focused with a lens 123 to an end of a fibre optic guide 124, which guides the excitation light beam to the optical measurement element 117. The fibre optic guide can be, for example, a bundle of fibres, such as 200 pieces of fibres with a diameter of e.g. 100 μm. The bundle of fibres can be used for mixing the excitation light beam in order to avoid an uneven distribution of light on a sample to be measured. The excitation light beam is reflected by a dichroic mirror 125 to a collimating lens 126. The excitation light beam is then focused with a lens 127 to the sample 153.

Photoluminescence emission beam from the sample 153 is directed with the lenses 127 and 126 to the dichroic mirror 125. The dichroic mirror is preferably designed so that it reflects excitation wavelength but transmits emission wavelengths. The emission beam is then divided into to two beams by a second mirror 128. The mirror 128 is preferably a dichroic mirror, which functions as a filter so that an emission beam with a first emission wavelength is transmitted through the mirror and an emission beam with a second emission wavelength is reflected by the mirror. The emission beam that is transmitted through the mirror 128 is collimated with a lens 129, filtered with an optical filter 130, and focused with a lens 131 into an aperture of a detector 132. The emission beam that is reflected by the mirror 128 is collimated with a lens 133, filtered with an optical filter 134, and focused with a lens 135 into an aperture of a detector 136. The detector 132 can be for example a photo-multiplier tube and the detector 136 can be for example a photo-diode. The detectors 132 and 136 are arranged to produce first and second detection signals responsive to the detected beam with the first emission wavelength and to the detected beam with the second emission wavelength. The first and second detection signals are then amplified and processed to achieve a value for the intensities of the emission beams with the first and second emission wavelengths. The optical measurement instrument includes a processing device 139 for producing a measurement result for each sample 151-157 to be measured on the basis of the detection signal related to the sample in question.

In the AlphaScreen™ measurement mode, the excitation light beam is received from an excitation light source 137 that is a laser source. The excitation light beam is guided via an optical guide 138 to the dichroic mirror 125. In the AlphaScreen™ measurement only one detector 132 is used, preferably a photomultiplier tube. In the AlphaScreen™ measurement a transparent thermo plate (not shown) is preferably used for sealing the openings of the sample wells 161-167.

Referring to FIG. 1a, the base module 100 includes one or more heating resistors arranged to warm the measurement chamber 170 and one or more temperature sensors arranged to produce one or more temperature signals responsive to temperature of the measurement chamber. The optical measurement instrument includes a controller 177 arranged to control electrical power supplied to the one or more heating resistors on the basis of the one or more temperature signals. Therefore, there is a closed control loop for regulating the temperature of the measurement chamber 170 and thus for keeping the samples 151-157 at an optimum measurement temperature. The controller 177 can be an integral part of the base module 100 or, alternatively, it can be a part of another portion of the optical measurement instrument. Arrows 179 in FIG. 1a represent one or more temperature signals produced by the one or more temperature sensors such as the temperature sensor 176 and arrows 178 represent one or more driving voltages of the one or more heating resistors. In the simplest implementation there is only one heating resistor and only one temperature sensor.

In an optical measurement instrument according to an embodiment of the invention, the base module 100 includes several heating resistors placed at different places of the measurement chamber 170 in order to provide a sufficiently spatially uniform temperature field in the measurement chamber. The heating resistors can be located, for example, on the lower surface of the second plate 103, as the heating resistors 171 and 172 shown in FIGS. 1a and 1c, and/or on the upper surface of the first plate 102, as the heating resistors 173, 174 and 175 shown in FIGS. 1a and 1b. It is also possible to use a resistive sheet that is arranged to cover a part or parts of the interior surfaces of the measurement chamber 170.

In an optical measurement instrument according to an embodiment of the invention, the controller 177 is arranged to control the electrical powers supplied to the heating resistors so that electrical power supplied to each heating resistor is proportional to a product of:
  a quantity q controlled on the basis of a temperature signal produced by a temperature sensor, and
  a balancing coefficient B specific to that particular heating resistor,
i.e. the electrical power supplied to the heating resistor is proportional to the product B×q. The electrical power supplied to each heating resistor can be e.g. linearly or square-law proportional to the product B×q. The electrical power of a heating resistor required for creating a certain thermal effect depends on the location of the heating resistor under consideration. A heating resistor surrounded by large mass requires more electrical power in order to create a same thermal effect than another heating resistor surrounded by smaller mass. Hence, different heating resistors may have different balancing coefficients in order to compensate the effect of differences in temperature/power-characteristics related to surroundings of the different heating resistors. The use of the balancing coefficients facilitates creating a sufficiently uniform thermal field especially in a situation in which the temperature is measured from only one point of the measurement chamber 170, i.e. only one temperature sensor is being used. For example, if a heating resistor $R_1$ has a balancing coefficient $B_1$ and a heating resistor $R_2$ has a balancing coefficient $B_2$, the electrical power supplied to $R_1$ can be proportional to $B_1 \times q$ and the electrical power supplied to $R_2$ can be proportional to $B_2 \times q$, where q is the quantity controlled on the basis of the temperature signal produced by the temperature sensor. The balancing coefficients can be used, for example, in such a manner the electrical power P supplied to a heating resistor R has the form P=B×q, where B is the balancing coefficient related to the heating resistor R. In this case, the electrical power of the heating resistor is linearly proportional to the product B×q. It is also possible to use the balancing coefficients in such a manner that the driving voltage u supplied to the heating resistor R has the form u=B×q. In this case, the electrical power of the heating resistor R is not linearly but square-law proportional to the product B×q, i.e. the electrical power is linearly proportional to $B^2 \times q^2$. The values of the balancing coefficients can be determined, for example, in such a manner that the temperature field of the measurement chamber is explored with e.g. a thermographic camera and the values of the balancing coefficients are tuned by trial and error until a sufficiently uniform temperature field is reached.

Figure 1C:
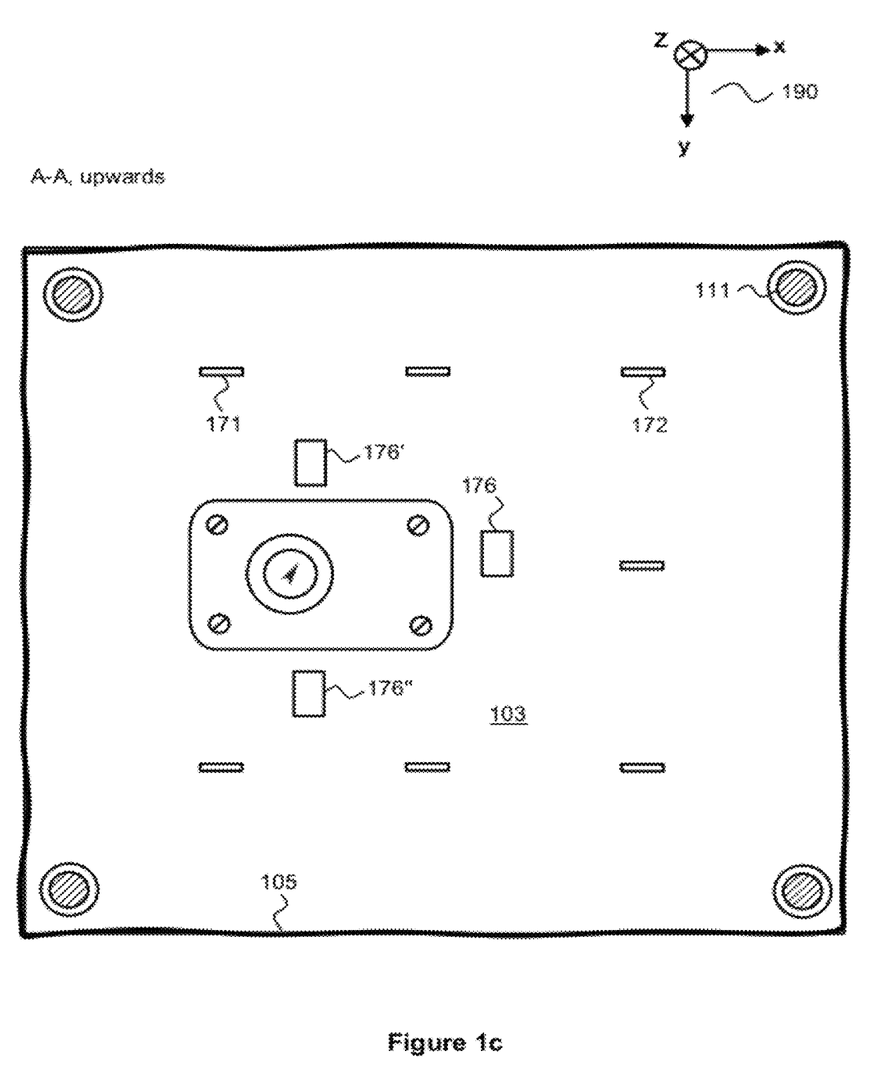

In an optical measurement instrument according to an embodiment of the invention, the base module 100 includes several temperature sensors at different places of the measurement chamber 107, and the controller 177 is arranged to control the electrical power of each heating resistor on the basis of a temperature signal given by one of the temperature sensors. Heating resistors, which are controlled on the basis of a temperature signal given by a certain temperature sensor, can be e.g. those heating resistors which are geometrically nearer to the said temperature sensor than to any other temperature sensor. In this case, the heating resistors are allocated into groups and each group is controlled with one of the temperature sensors. Furthermore, the electrical power supplied to each heating resistor can be controlled to be proportional to a balancing coefficient specific to that particular heating resistor. For example, if heating resistors $R_1$ and $R_2$ are controlled with a same temperature sensor and the heating resistor $R_1$ has a balancing coefficient $B_1$ and the heating resistor $R_2$ has a balancing coefficient $B_2$, the electrical power supplied to $R_1$ can be proportional to $B_1 \times q$ and the electrical power supplied to $R_2$ can be proportional to $B_2 \times q$, where q is the quantity controlled on the basis of the temperature signal produced by the said temperature sensor. The base module of the optical measurement instrument illustrated in FIGS. 1a-1c includes temperature sensors 176, 176' and 176" located on the lower surface of the second plate 103. The temperature sensor 176 is shown in FIG. 1a and in FIG. 1c that shows a schematic illustration of a view seen upwards from the line A-A of FIG. 1a, and the temperature sensors 176' and 176" are shown in FIG. 1c.

In an optical measurement instrument according to an embodiment of the invention, the controller 177 is arranged to control the driving voltage of each of the one or more heating resistors with the pulse width modulation (PWM) in order to control the electrical power of that heating resistor.

In an optical measurement instrument according to an embodiment of the invention, the controller 177 is arranged to operate as a proportional-integrative-derivative (PID) regulator for controlling the electrical power supplied to each of the one or more heating resistors on the basis of the one or more temperature signals given by the one or more temperature sensors. For example, if electrical powers supplied to heating resistors $R_1$ and $R_2$ are controlled on the basis of a temperature signal T and the heating resistor $R_1$ has a balancing coefficient $B_1$ and the heating resistor $R_2$ has a balancing coefficient $B_2$, the electrical power supplied to $R_1$ can be proportional to $B_1 \times q$ and the electrical power supplied to $R_2$ can be proportional to $B_2 \times q$, wherein the quantity q is PID-controlled on the basis of the difference between T and a reference temperature $T_{ref}$.

Figure 2:
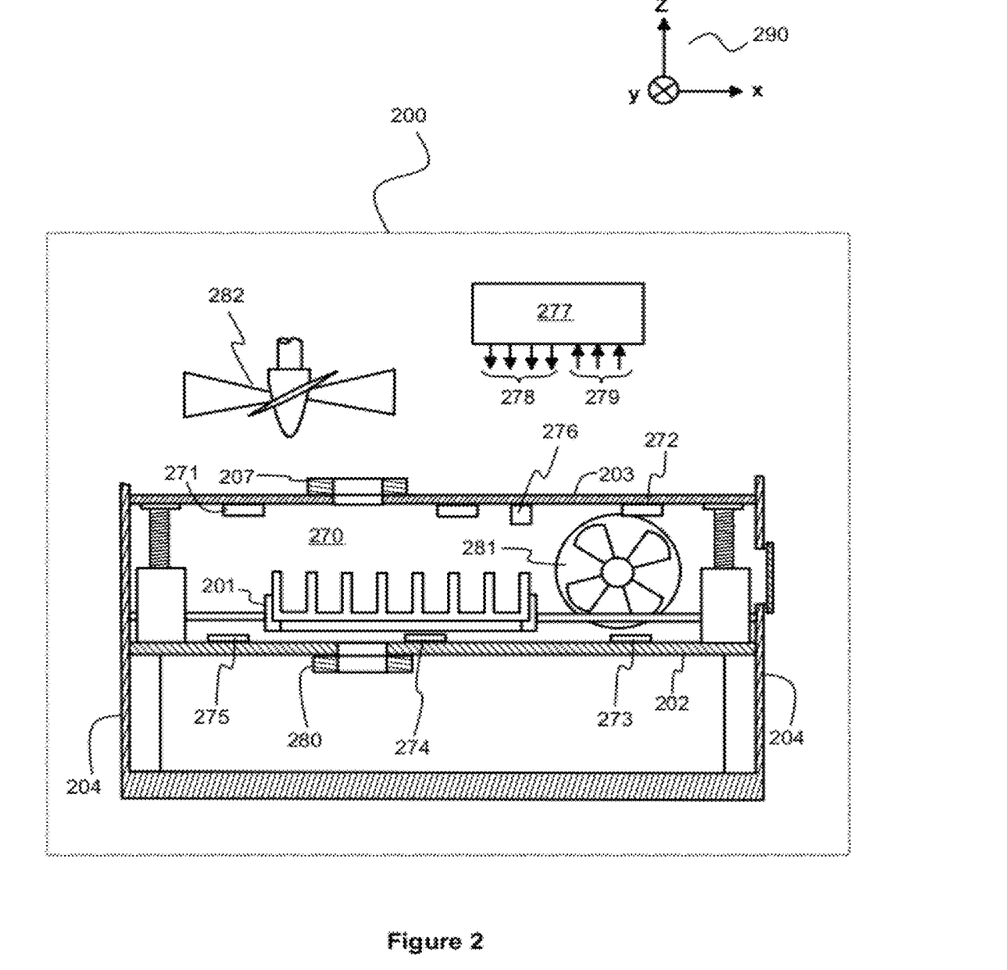

FIG. 2 shows a schematic illustration of a section view of a base module 200 according to an embodiment of the invention. The base module includes a mechanical structure forming a measurement chamber 270. The mechanical structure forming the measurement chamber includes a first plate 202, a second plate 203 substantially parallel with the first plate and movably supported with respect to the first plate. The second plate is movable in a direction substantially perpendicular to the first and second plates, i.e. the second plate is movable in the positive and negative z-direction of the co-ordinate system 290. The mechanical structure forming the measurement chamber further includes walls 204 extending from outer edges of the first plate to outer edges of the second plate. The second plate 203 includes at least one fastening interface 207 suitable for an optical measurement element to be mounted to the second plate. Also the first plate 202 may include at least one fastening interface 280 suitable for an optical measurement element to be mounted to the first plate. The base module includes a reception device 201 inside the measurement chamber for receiving samples to be measured. The base module further includes one or more heating resistors 271, 272, 273, 274 and 275 arranged to warm the measurement chamber 270, and one or more temperature sensors 276 arranged to produce one or more temperature signals responsive to temperature of the measurement chamber.

A base module according to an embodiment of the invention further comprises a controller 277 arranged to control electrical power supplied to each of the one or more heating resistors on the basis of the one or more temperature signals produced by the one or more temperature sensors 276. Arrows 279 in FIG. 2 represent one or more temperature signals produced by the one or more temperature sensors and arrows 278 represent one or more driving voltages of the one or more heating resistors.

In a base module according to an embodiment of the invention, the controller 277 is arranged to control the electrical powers supplied to the heating resistors so that the electrical power supplied to a first one of the heating resistors is proportional to $B_1 \times q$ and the electrical power supplied to a second one of the heating resistors is proportional to $B_2 \times q$, wherein q is a quantity controlled on the basis of a certain temperature signal, $B_1$ is a pre-determined balancing coefficient specific to the first one of the heating resistors, and $B_2$ is a pre-determined balancing coefficient specific to the second one of the heating resistors. The balancing coefficient $B_1$ may have a different value than the balancing coefficient $B_2$ in order to compensate the effect of differences in temperature/power-characteristics related to surroundings of the first and second ones of the heating resistors.

A base module according to an embodiment of the invention comprises temperature sensors placed at different places of the measurement chamber. In a base module according to an embodiment of the invention, the controller 277 is arranged to control the electrical power supplied to each of the heating resistors on the basis of a temperature signal produced by a particular temperature sensor that, from among all the temperature sensors, is nearest to the heating resistor under consideration.

A base module according to an embodiment of the invention comprises a blower 282 arranged to blow cooling air towards outer walls of the measurement chamber 270. In a base module according to an embodiment of the invention, the controller 277 is arranged to control the operation of the blower on the basis of the one or more temperature signals. For example, if there are more than one temperature signals, the operation of the blower can be controlled e.g. on the basis of an arithmetic average of the temperature signals or on the basis of the maximum of temperatures indicated by the temperature signals.

A base module according to an embodiment of the invention comprises a blower 281 arranged to blow cooling air into the measurement chamber. In a base module according to an embodiment of the invention, the controller 277 is arranged to control the operation of the blower on the basis of the one or more temperature signals.

Figure 3:
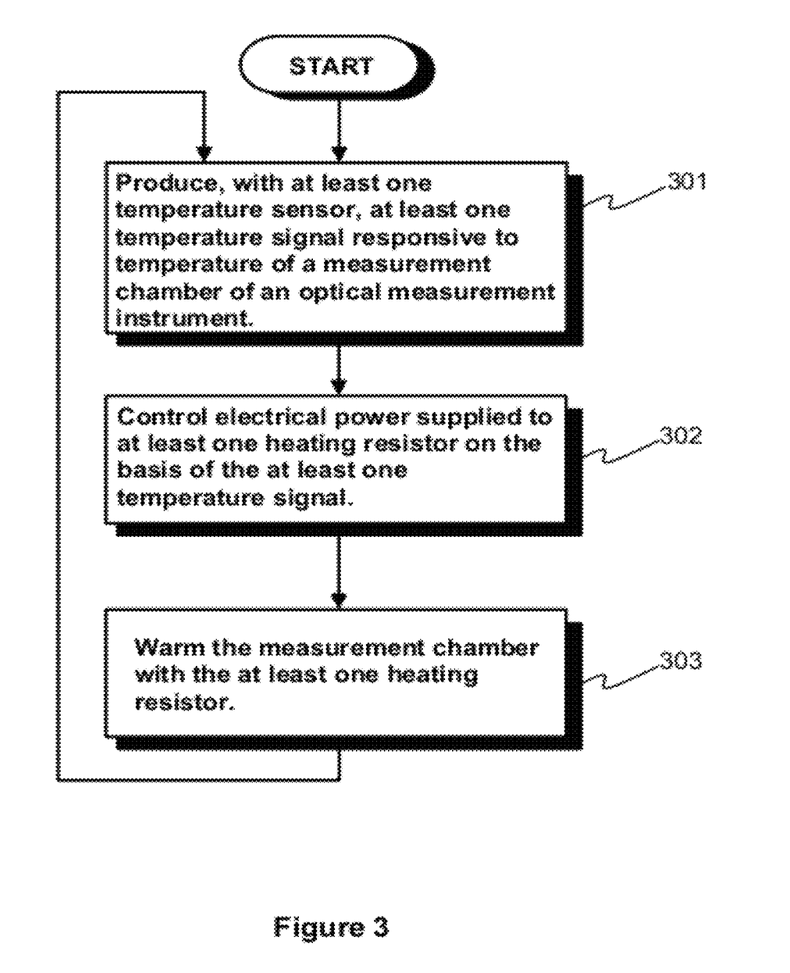
FIG. 3 shows a flow chart of a method according to an embodiment of the invention for controlling temperature of samples being measured with an optical measurement instrument.

FIG. 3 shows a flow chart of a method according to an embodiment of the invention for controlling temperature of samples being measured with an optical measurement instrument. The method comprises:

producing, in a phase 301 using one or more temperature sensors, one or more temperature signals responsive to temperature of a measurement chamber of the optical measurement instrument, the samples being located in the measurement chamber, controlling, in a phase 302, electrical power supplied to one or more heating resistors on the basis of the one or more temperature signals, and warming, in a phase 303, the measurement chamber with the one or more heating resistor.

In a method according to an embodiment of the invention, the measurement chamber is warmed with many heating resistors placed at different places of the measurement chamber in order to create a sufficiently uniform temperature field in the measurement chamber.

In a method according to an embodiment of the invention, the electrical powers supplied to the heating resistors are controlled so that the electrical power supplied to a first one of the heating resistors is proportional to $B_1 \times q$ and the electrical power supplied to a second one of the heating resistors is proportional to $B_2 \times q$, wherein q is a quantity controlled on the basis of a certain temperature signal, $B_1$ is a pre-determined balancing coefficient specific to the first one of the heating resistors, and $B_2$ is a pre-determined balancing coefficient specific to the second one of the heating resistors. The balancing coefficient $B_1$ may have a different value than the balancing coefficient $B_2$ in order to compensate effect of differences in temperature/power-characteristics related to surroundings of the first and second ones of the heating resistors.

In a method according to an embodiment of the invention, the at least one temperature sensor includes temperature sensors placed at different places of the measurement chamber and the electrical power supplied to each of the heating resistors is controlled on the basis the temperature signal produced by the particular temperature sensor nearest to the heating resistor under consideration.

A method according to an embodiment of the invention further comprises controlling a blower arranged to blow cooling air towards outer walls of the measurement chamber on the basis of the one or more temperature signals.

A method according to an embodiment of the invention further comprises controlling a blower arranged to blow cooling air into the measurement chamber on the basis of the one or more temperature signals.

In a method according to an embodiment of the invention, the electrical power of each heating resistor is controlled by controlling driving voltage of that heating resistor with the pulse width modulation (PWM).

In a method according to an embodiment of the invention, the electrical power of each heating resistor is controlled with a proportional-integrative-derivative (PID) regulator on the basis of the one or more temperature signals. For example, if electrical powers supplied to heating resistors $R_1$ and $R_2$ are controlled on the basis of a temperature signal T and the heating resistor $R_1$ has a balancing coefficient $B_1$ and a heating resistor $R_2$ has a balancing coefficient $B_2$, the electrical power supplied to $R_1$ can be proportional to $B_1 \times q$ and the electrical power supplied to $R_2$ can be proportional to $B_2 \times q$, wherein the quantity q is PID-controlled on the basis of the difference between T and a reference temperature $T_{ref}$.

The specific examples provided in the description given above should not be construed as limiting. Therefore, the invention is not limited merely to the embodiments described above.

What is claimed is:

1. A base module for an optical measurement instrument, the base module comprising:
   a mechanical structure for forming a measurement chamber and for supporting one or more optical measurement elements,
   a reception device inside the measurement chamber for receiving samples to be measured,
   heating resistors placed at different places of the measurement chamber, each heating resistor being arranged to warm the measurement chamber,
   at least one temperature sensor, each temperature sensor being arranged to produce a temperature signal responsive to temperature of the measurement chamber, and
   a controller arranged to control electrical power supplied to each of the at least one heating resistor on the basis of the at least one temperature signal produced by the at least one temperature sensor,
   wherein the controller is arranged to control the electrical powers supplied to the heating resistors so that the electrical power supplied to a first one of the heating resistors is proportional to $B_1 \times q$ and the electrical power supplied to a second one of the heating resistors is proportional to $B_2 \times q$, wherein q is a quantity controlled on the basis of one of the at least one temperature signal, $B_1$ is a pre-determined balancing coefficient specific to the first one of the heating resistors, and $B_2$ is a pre-determined balancing coefficient specific to the second one of the heating resistors, the balancing coefficient $B_1$ having a different value than the balancing coefficient $B_2$ in order to compensate effect of differences in temperature/power-characteristics related to surroundings of the first and second ones of the heating resistors.

2. A base module according to claim 1, wherein the at least one temperature sensor comprises temperature sensors placed at different places of the measurement chamber and the controller is arranged to control the electrical power supplied to each of the heating resistors on the basis the temperature signal produced by the particular temperature sensor nearest to that heating resistor.

3. A base module according to claim 2, wherein the base module comprises a blower arranged to blow cooling air towards outer walls of the measurement chamber.

4. A base module according to claim 1, wherein the base module comprises a blower arranged to blow cooling air towards outer walls of the measurement chamber.

5. A base module according to claim 1, wherein the base module comprises a blower (281) arranged to blow cooling air into the measurement chamber.

6. A base module according to claim 1, wherein the mechanical structure for forming the measurement chamber comprises:
   a first plate,
   a second plate substantially parallel with the first plate and movably supported with respect to the first plate, the second plate being movable in a direction substantially perpendicular to the first and second plates, and
   walls extending from outer edges of the first plate to outer edges of the second plate,
   wherein the measurement chamber is constituted by the walls and the first and second plates and the second plate comprises at least one fastening interface suitable for an optical measurement element to be mounted to the second plate.

7. A base module according to claim 6, wherein at least one of the at least one heating resistor is mounted on the surface of the first plate.

8. A base module according to claim 7, wherein at least one of the at least one heating resistor is mounted on the surface of the second plate.

9. A base module according to claim 6, wherein at least one of the at least one heating resistor is mounted on the surface of the second plate.

10. A base module according to claim 1, wherein the controller is arranged to control driving voltage of each of the at least one heating resistor with pulse width modulation (PWM) for controlling the electrical power of that heating resistor.

11. A base module according to claim 1, wherein the controller is arranged to operate as a proportional-integrative-derivative (PID) regulator for controlling the electrical power supplied to each of the at least one heating resistor on the basis of the at least one temperature signal produced by the at least one temperature sensor.

12. A base module according to claim 1, wherein,
   the base module comprises said first and second heating resistors and a first said temperature sensor, said first and second heating resistors being controlled by said first temperature sensor,
   the controller arranged to control the electrical power supplied to said first heating resistor on the basis of the one temperature signal produced by the first temperature sensor,
   wherein the controller is arranged to control the electrical powers supplied to the first and second heating resistors so that
   i) the electrical power supplied to the first heating resistor is proportional to $B_1 \times q$, and
   ii) the electrical power supplied to the second heating resistor is proportional to $B_2 \times q$,
   wherein q is the quantity controlled on the basis of the one temperature signal of the first temperature sensor,
   $B_1$ is the pre-determined balancing coefficient specific to the first heating resistor, $B_2$ is the pre-determined balancing coefficient specific to the second heating resistor, and the balancing coefficients of $B_1$ and $B_2$ compensate for the effect of the differences in the temperature characteristics and the power-characteristics of the surroundings of the first and second heating resistors, and respectively depend on the temperature characteristics and the power-characteristics of the surroundings of the first and second heating resistors.

13. An optical measurement instrument comprising optical measurement elements and a base module, at least one of the optical measurement elements including an excitation light source arranged to produce an excitation beam for at least one of samples to be measured, and at least one of the optical measurement elements including a detector arranged to detect an emission beam emitted by one of the samples to be measured and to produce a detection signal responsive to the detected emission beam, and the base module comprising:

a mechanical structure for forming a measurement chamber, a reception device inside the measurement chamber for receiving the samples to be measured, heating resistors placed at different places of the measurement chamber, each heating resistor being arranged to warm the measurement chamber, at least one temperature sensor, each temperature sensor being arranged to produce a temperature signal responsive to temperature of the measurement chamber, and a controller arranged to control electrical power supplied to each of the at least one heating resistor on the basis of the at least one temperature signal produced by the at least one temperature sensor, wherein at least one of the optical measurement elements is mounted to the mechanical structure forming the measurement chamber and the controller is arranged to control the electrical powers supplied to the heating resistors so that the electrical power supplied to a first one of the heating resistors is proportional to $B_1 \times q$ and the electrical power supplied to a second one of the heating resistors is proportional to $B_2 \times q$, wherein q is a quantity controlled on the basis of one of the at least one temperature signal, $B_1$ is a pre-determined balancing coefficient specific to the first one of the heating resistors, and $B_2$ is a pre-determined balancing coefficient specific to the second one of the heating resistors, the balancing coefficient $B_1$ having a different value than the balancing coefficient $B_2$ in order to compensate effect of differences in temperature/power-characteristics related to surroundings of the first and second ones of the heating resistors.

14. A method for controlling temperature of samples being measured with an optical measurement instrument, the method comprising:

producing, with at least one temperature sensor, a temperature signal responsive to temperature of a measurement chamber of the optical measurement instrument, the samples being located in the measurement chamber, controlling electrical powers supplied to heating resistors placed at different places of the measurement chamber on the basis of the temperature signal, and warming the measurement chamber with the heating resistors, wherein the electrical powers supplied to the heating resistors are controlled so that the electrical power supplied to a first one of the heating resistors is proportional to $B_1 \times q$ and the electrical power supplied to a second one of the heating resistors is proportional to $B_2 \times q$, wherein q is a quantity controlled on the basis of one of the at least one temperature signal, $B_1$ is a pre-determined balancing coefficient specific to the first one of the heating resistors, and $B_2$ is a pre-determined balancing coefficient specific to the second one of the heating resistors, the balancing coefficient $B_1$ having a different value than the balancing coefficient $B_2$ in order to compensate effect of differences in temperature/power-characteristics related to surroundings of the first and second ones of the heating resistors.

\* \* \* \* \*